United States Patent [19]

Fischer

[11] Patent Number: 5,347,894

[45] Date of Patent: Sep. 20, 1994

[54] TORQUE LIMITING DEVICE

[75] Inventor: Paul D. Fischer, Bloomington, Minn.

[73] Assignee: PMT Corporation, Chanhassen, Minn.

[21] Appl. No.: 69,160

[22] Filed: May 28, 1993

[51] Int. Cl.⁵ ............................................. B25B 23/153
[52] U.S. Cl. ......................................... 81/471; 81/467; 606/104
[58] Field of Search ....................... 81/467, 471, 436; 606/53, 54, 59, 86, 104; 602/17, 18, 37

[56] References Cited

U.S. PATENT DOCUMENTS

| | | |
|---|---|---|
| 1,398,842 | 11/1921 | Cruse . |
| 2,740,315 | 3/1956 | Gouverneur II . |
| 3,072,118 | 1/1963 | Standerwick et al. . |
| 3,331,267 | 7/1967 | Tietge . |
| 3,391,693 | 7/1968 | Georgiade et al. . |
| 3,604,412 | 9/1971 | Gardner . |
| 3,669,102 | 6/1972 | Harris . |
| 3,923,046 | 12/1975 | Heifetz . |
| 4,215,680 | 8/1980 | Kesselman . |
| 4,251,600 | 8/1980 | Kesselman . |
| 4,612,930 | 9/1986 | Bremer . |
| 4,667,660 | 5/1987 | Eingorn . |
| 4,833,951 | 5/1989 | Karcher et al. ............. 81/471 |
| 4,838,264 | 6/1989 | Bremer et al. . |
| 5,158,458 | 10/1992 | Perry ............................ 81/471 X |
| 5,176,050 | 1/1993 | Sauer et al. .................... 81/471 |

FOREIGN PATENT DOCUMENTS

| | | |
|---|---|---|
| 2231949 | 2/1973 | Fed. Rep. of Germany ........ 81/471 |
| 3538593 | 5/1987 | Fed. Rep. of Germany . |
| 2486852 | 7/1980 | France . |
| 854792 | 11/1960 | United Kingdom . |

OTHER PUBLICATIONS

Guard–Nut Torque Limiter; May 1980 Pamphlet; 20450 Broadway, Drawer 299, Sonoma, Calif. 95476.

Primary Examiner—Richard J. Apley
Assistant Examiner—Linda C. M. Dvorak
Attorney, Agent, or Firm—Palmatier, Sjoquist & Helget

[57] ABSTRACT

The present invention relates to a torque limiting device for use in the affixation of a halo-type traction tool to the skull of a person. The torque limiting device has a shaft or shank embedded in a handle member which rotatably engages a skull pin during the fixation of a halo-type traction device to an individual. The torque limiting device has a first shear point at a reduced shank intermediate portion which prevents rotational torque forces in excess of a predetermined level from being applied to a skull pin during the attachment procedure of a medical cervical traction brace or tool. The present invention also includes a second shear point at the shank-handle interface which acts as a second safety mechanism to ensure that excessive pressure is not applied, and undesirable skull penetration does not occur, during the attachment procedure of a skull pin and halo to an individual's skull. The torque limiting device further includes a skull pin engaging end. The handle encapsulates a substantial portion of the shank, including the first and second shear points, and a handle-shank interface retaining collar and groove arrangement from which the pin engaging end extends also from the handle. Upon release of the first shear point or the second shear point, the handle and skull pin engaging end may rotate free of each other without separation of the handle from the skull pin engaging end, thereby keeping the device in one piece for easy handling, loss prevention and protecting an individual from risk of injury.

33 Claims, 1 Drawing Sheet

TORQUE LIMITING DEVICE

BACKGROUND OF THE INVENTION

Individuals may receive severe head and spinal cord injuries necessitating the use of halo-type traction tools, braces and devices for the treatment of their injuries. The use of halo-type cervical traction devices is known and described in U.S. Pat. No. 3,072,118 to R. G. Standerwick, et al.

Generally, a plurality of anchoring devices are required to be attached to the halo-type traction tool or brace which typically is anchored to the bone of an individual's skull, during the treatment of spinal fractures or injuries and facial reconstruction surgery. Various types of halo and anchoring tools and devices are known, an example of which includes U.S. Pat. No. 4,838,264 to Bremer, et al. Generally, anchoring bone-penetrating skull pins are set in the halo and rotatably driven axially into the skull bone with a torque device in order to affix a halo-type traction tool to an individual's skull for anchoring further devices.

It is important to note that severe injury may occur if the skull pin goes into the skull too far. Bremer's skull pins have attempted to implement a torque sensitive safety feature which includes the shearing of the handle from the pin engaging cap upon reaching to a predetermined level of torque. This shearing action results in two pieces of the torque limiting device.

There is a need for a torque limiting device for use and in combination with skull pins and halo-traction tools which has not one, but two, shear safety features to prevent skull penetration by the pin or screw causing severe injury. Such a torque limiting device should also remain in one piece for easy handling by the surgeon and also to prevent lose of component parts which is problematic with the prior art.

SUMMARY OF THE INVENTION

The present invention relates to a torque limiting device for use in the affixation of a halo-type traction tool to the skull of a person. The torque limiting device has a shaft or shank embedded in a handle member which rotatably engages a skull pin during the fixation of a halo-type traction device to an individual. The torque limiting device has a first shear point at a reduced shank intermediate portion which prevents rotational torque forces in excess of a predetermined level from being applied to a skull pin during the attachment procedure of a medical cervical traction brace or tool. The present invention also includes a second shear point at the shank-handle interface which acts as a second safety mechanism to ensure that excessive pressure is not applied, and undesirable skull penetration does not occur, during the attachment procedure of a skull pin and halo to an individual's skull. The torque limiting device further includes a skull pin engaging end. The handle encapsulates a substantial portion of the shank, including the first and second shear points, and a handle-shank interface retaining means from which the shank pin engaging end extends also from the handle. Upon release of the first shear point or the second shear point, the handle and skull pin engaging end may rotate free of each other without separation of the handle from the skull pin engaging end, thereby keeping the device in one piece for easy handling, loss prevention and protecting an individual from risk of injury.

It is a principal object of the present invention to provide a new and improved torque limiting device and skull pin assembly of relatively simple and inexpensive design, construction, and operation. The assembly is safe, durable, dependable and fulfills the intended purpose without fear of injury to the skull or brain of a person.

It is another object of the present invention to provide a surgeon with a torque limiting device, which includes a primary safety feature and a secondary safety feature, thereby further minimizing the risk of excessive torque forces to an individual's skull as heretofore not known.

It is another object of the present invention to provide a torque limiting device which continues to remain intact in one piece following shearing at the first and second shearing points for easy handling and loss prevention.

A feature of the present invention includes a one-piece T-shaped polycarbonate handle engaged to a metallic shank.

Still another feature of the present invention includes a skull pin having a point, a threaded shaft, and a head having a hexagonal shaped cavity for engagingly receiving the tool engaging end portion of the torque limiting device.

Other objects, advantages and features will become apparent upon a review of the figures, following specification and appended claims.

DETAILED SPECIFICATION OF THE PREFERRED EMBODIMENT

Figure 1:
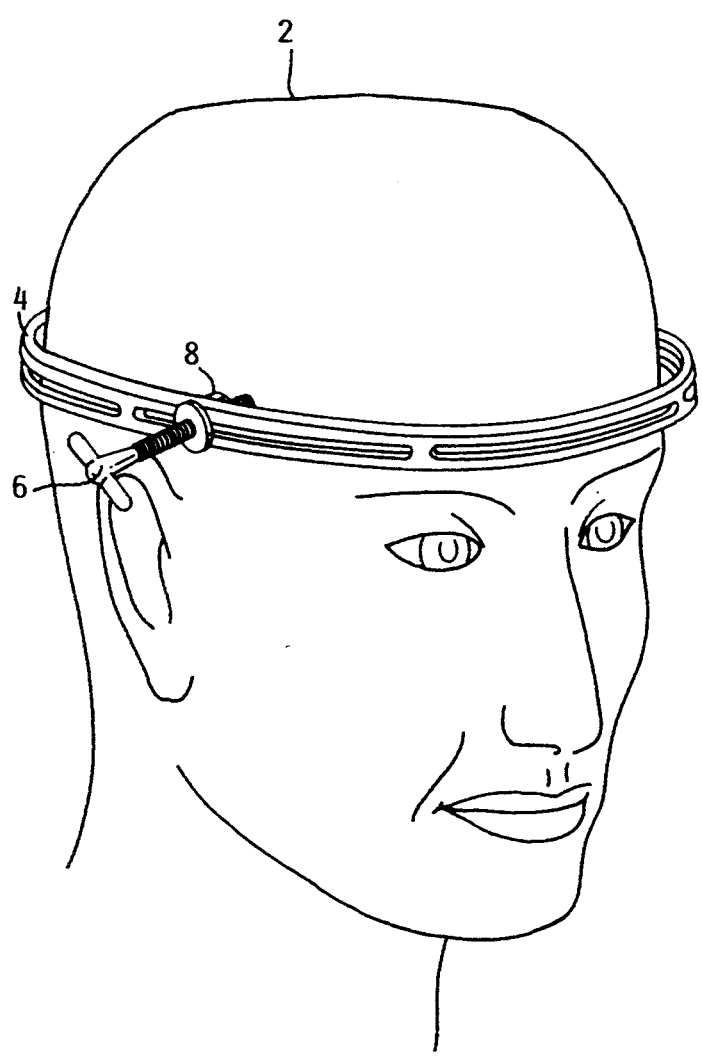
FIG. 1 is an isometric view of the invention engaged to a halo traction tool and to an individual's skull.
Figure 2:
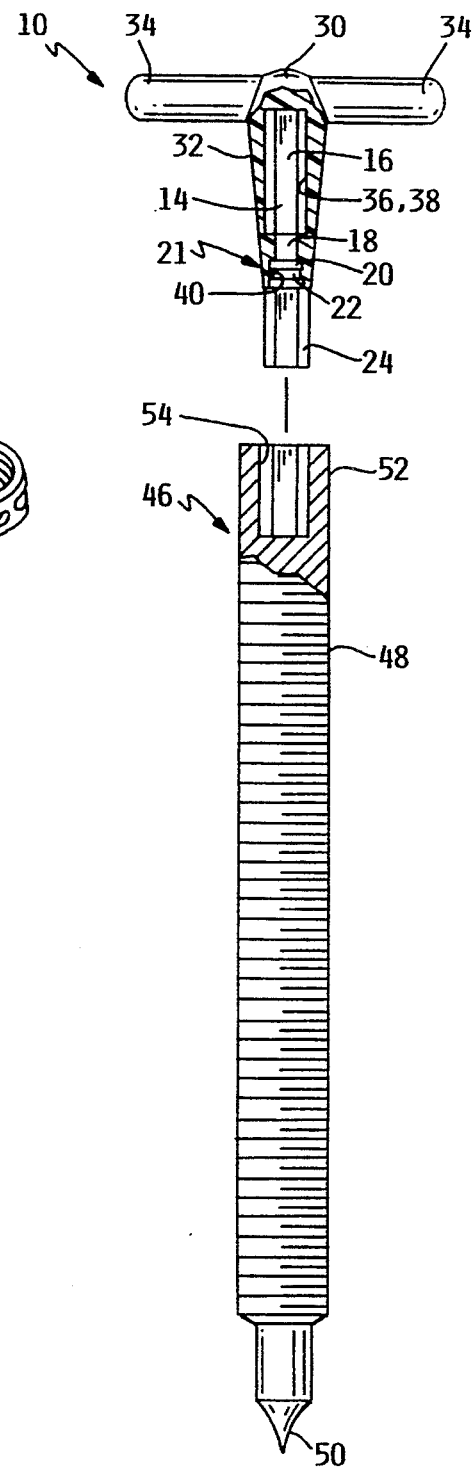
FIG. 2 is a front elevational view of the torque limiting device and skull pin partially cutaway for ease of understanding.

FIG. 1 shows a human head or skull 2, with a halo traction tool 4 therearound and affixed thereat by skull pins 6 further affixed to the halo 4 by lock nuts 8. Halo 4 may take any of a variety of shapes. In general, the torque limiting device is indicated by the numeral 10. The torque limiting device 10 is generally used with a medical tool, such as a halo-type traction device 4 (FIG. 1). The torque limiting device 10 generally includes a rod, shaft or shank 14 substantially embedded in a handle 30 which rotatably drives a bone-penetrating skull pin or screw 46 to secure the tool or halo 4 to the skull 2 (FIG. 2).

The rod, shaft or shank 14 is generally of one piece construction and is preferably, but only illustratively, formed of brass metal material having a specific alloy mixture of 61.5% copper, 35.5% zinc, and 3.0% lead. This composition has shown to be predictably dependable for this application. The shank 14 generally includes a cross-sectionally configured handle end portion 16, a round or cylindrically configured intermediate first shearing portion 18, a retaining collar 20 with groove or channel 22, and a cross-sectionally configured tool engaging end portion 24.

The handle end portion 16 of the shank 14 is preferably configured, such as hexagonal in shape. The handle end portion 16 encapsulated within the interior 36 of the handle 16 functions as the strippable second shearing point 38 discussed further below.

The intermediate shearing portion 18 of the shank 14 depends from handle end portion 16 and is preferably cylindrical in shape. The intermediate shearing portion 18 functions as the location of, and defines, a first shear point for the torque limiting device 10. The cross-sectional dimension of the intermediate shearing portion 18 is suitably smaller than the handle end portion 16 in order to facilitate the shear of the torque limiting device 10 at the first shear point 18. Preferably, the shearing portion 18 shears at the first shear point upon the application of a rotational torque force to the handle 30 and the skull screw 46 equal to, or greater than, a preselected level. The shearing of the intermediate shearing portion 18, at the first shear point, prevents further axial advancement of the bone penetrating screw 46 into the bone of a cranium or skull during affixation of a halo traction system or tool 4.

The shank-handle interface retaining means 21 suitably includes the retaining collar 20. Collar 20 is preferably cylindrical in shape and has a groove, annular slot or channel 22 encircling its entire circumference. The retaining collar 20 functions as a location for the rotational engagement between the skull pin or tool engaging end portion 24 of shank 14 and the handle 30 following the shear of the intermediate shearing portion 18 at the first shear point. The entire circumference of the retaining collar 20 is preferably integrally encapsulated within the interior 36 of the handle 30. The handle 30 may then have an internal retaining ring portion 40 fit or molded in channel 22. This arrangement permits handle 30 rotation about the retaining collar 20, via the ring 40 seating in the channel or groove 22, following shear of the first shear point or intermediate portion 18. The channel 22 and handle ring portion 40 provide the mechanism for maintaining the torque limiting device 10 in an intact single unit configuration following the shear of the shearing portion 18, which separates the handle end portion 16 from the retaining collar 20. It should be noted that the collar 20 and channel 22 structure may be on the inside 36 of handle 30 with the ring 40 structure being on the shank 14.

The tool engaging portion 24 is suitably configured, such as hexagonal, and functions as the portion of the shank 14 for rotatable engagement with the bone penetrating skull screw 46 and halo 4 assembly. The tool engaging end portion 24 is integral with, and depends from, the retaining collar 20. It should be noted that the handle control body portion 32 terminates just at or slightly beyond the retaining collar 20 proximal to the tool engaging end portion 24. The tool engaging portion 24 is not encapsulated within the interior of the handle 16 as to not interfere with its engagement with the skull pin 46.

The handle member 30 is preferably T-shaped and is formed of polycarbonate or plastic material. The handle 30 has a central body portion 32 and preferably two outwardly diverging grasping members or pegs 34. The interior 36 of the handle 30 interfaces with and engages the handle end portion 16 to define a shearable handle-shank interface 38 or the second shear point 38 for the torque limiting device 10. The second shear point 38 acts as a safety shear alternative to the first shear point or the intermediate shearing portion 18 of the shank 14. The cylindrically configured intermediate shearing portion 18 with the retaining collar 20 of the shank 14 are encapsulated within the interior 36 of the handle 30. If the torque limiting device 10 does not shear at the first shear point 18, then the hexagonal shaped handled end portion 16 shears at the interior handle-shank interface 38 of the polycarbonate handle 30 or the second shear point 38, upon the application of a preselected level of rotational torque force.

If the torque limiting device 10 shears along the first or second shear points 18 and 38, then the handle 30 still advantageously rotates about the retaining collar 20 due to the internal ring-channel seating engagement of the handle retaining ring 40 molded into the channel or groove 22. The handle 30 therefore rotates about the retaining collar 20 and channel 22 regardless of the shearing of the first shear point 18 or the second shear point 38. Thus, the halo-ed individual is protected from the risk of undesirable skull penetration while the device 10 still remains in one piece. This one piece offers obvious advantages in handling and loss prevention of the device 10. Again, it is to be noted that the retaining ring 40 and collar 20 with groove 22 may be reversed from the shank 14 and handle interior 36 with equivalent function.

The bone penetrating skull screw pin or tool 46 preferably includes a threaded shaft 48, a skull-engaging point 50, and a head 52 having a configured, such as hexagonal shaped, cup or cavity 54 commonly used with allen wrenches and engageable with engaging end 24 of shank 14. The threaded shaft 48 may be threaded into the halo 4. The bone penetrating skull screw 46 is preferably formed of titanium metal and/or stainless metal material. The point 50 of the skull screw 46 is preferably adapted for engagement to the cranial bone of an individual. The material of the point 50 is required to be of sufficient strength and hardness to not fracture or break during use with a halo-type traction system 4. This material may be metal or ceramic. The threaded shaft 48 of the skull screw 46 is required to be of sufficient strength and durability to not fracture, break or fail during the positioning of the halo-type traction device or tool 4 proximal to the skull of an individual.

The cavity 54 is preferably adapted for receiving engagement of the tool engaging end portion 24 of the shank 14. The torque limiting device 10 may then be rotated in either a clockwise or counterclockwise direction for adjustment or positioning of a halo-type traction device 4 upon the skull 2 of an individual. Thereafter, locking nuts 8 may be used to fixedly secure the screw 46 to the tool or halo 4.

As stated, the shank 14, handle end portion 16, intermediate shearing portion 18, retaining collar 20, and tool engaging end portion 24, are all integrally formed of brass metal material in order to provide a uniform and consistent material for predictability of the shearing portion 18, which is to repeatedly and predictably shear upon the application of a predetermined selected torque force.

In operation, when the torque limiting device 10 is exposed to the preselected level of torque, the first shear point 18 or the intermediate shearing portion 18 fails, separating the handle end portion 16 from the shank-handle interface retaining means 21 (channel 22 and ring 40). Rotation of the handle inner surface retaining ring 40 then occurs in the channel 22 of collar 20 without rotation of the tool engaging end portion 24. Additional rotational torque to and axial penetration of the skull screw 46 has ceased.

Alternatively, the second shear point 38, acting as a secondary safety, will fail at a predetermined torque limit thereby stripping and separating the interface 38 between handle end portion 16 of shank 14. Rotation of the handle 30 and retaining ring 40 then occurs about the retaining collar 20 and groove 22 without rotation of the tool engaging end 24. Termination of the additional rotational torque, and penetrating of, the skull screw 18 also then occurs.

It again should be noted that the handle 30 and shank 14 remain as an integral one-piece unit regardless of the shearing of the first shear point 18 or the second shear point 38. The handle 30 may then be retracted, separating the tool engaging end portion 24 from the cavity 54 of pin 46. The handle 30 and the shank 14 may then be properly disposed of while the skull screw 46 remains fixedly positioning the halo-type traction device 4 upon the skull of an individual.

The present invention may be embodied in other specific forms without departing from the spirit or essential attributes thereof; therefore, the illustrated embodiment should be considered in all respects as illustrative and not restrictive, reference being made to the appended claims rather than to the foregoing description to indicate the scope of the invention.

What is claimed:

1. A torque limiting device for applying rotational force to a medical related tool, comprising:
   (a) a shank having a handle end portion, an intermediate shearing portion, and a tool engaging end portion, the intermediate shearing portion is adapted to shear the shank into two pieces at a determined rotational force;
   (b) a handle grippable by a human hand encapsulating the handle end portion and the intermediate shearing portion to apply rotational force to the tool through the device; and
   (c) a retaining interface means between the handle and the shank encapsulated by the handle adjacent the tool engaging end portion as to keep the device in one piece upon shearing of the intermediate portion of the shank.

2. The torque limiting device of claim 1, wherein the handle end portion and tool engaging end portion have a cross-sectional configuration other than cylindrical while the cross-sectional configurations of the intermediate shearing portion and the retaining interface means are cylindrical.

3. The torque limiting device of claim 2, wherein the handle end portion of the shank and the encapsulating handle interface therewith form a second strippable shearing portion.

4. The torque limiting device of claim 1, wherein the handle is made of plastic.

5. The torque limiting device of claim 1, wherein the shank is made of brass.

6. The torque limiting device of claim 1, wherein the shank is integrally one piece.

7. The torque limiting device of claim 1, wherein the retaining interface means comprises a rotatably interlockable protruding ring and annular channel arrangement between the handle and the shank.

8. The torque limiting device of claim 7, wherein the ring is on the handle and the channel is on the shank.

9. The torque limiting device of claim 7, wherein the ring is on the shank and the channel is on the handle.

10. The torque limiting device of claim 7, wherein the annular channel is surrounded by a collar.

11. The torque limiting device of claim 1, wherein the grippable handle is T-shaped with outwardly extending pegs.

12. The torque limiting device of claim 1, wherein the tool engaging end portion is engageable for rotation with a head of a screw for mounting the medical related tool to an individual.

13. The torque limiting device of claim 12, wherein the tool engaging end has a cross-sectional configuration other than cylindrical.

14. The torque limiting device of claim 13, wherein the head of the screw has a cup the interior of which is cross-sectionally configured to rotatably interlock with the tool engaging end upon insertion of the tool engaging end into the cup.

15. The torque limiting device of claim 1, wherein the medically related tool comprises a halo traction device affixable to a human head with skull screws.

16. A torque limiting device for applying rotational force to a medical related tool, comprising:
   (a) a metallic, integral shank having a handle end portion, an intermediate shearing portion, and a tool engaging end portion, the intermediate shearing portion is adapted to shear the shank into two pieces at a determined rotational force;
   (b) a plastic handle grippable by a human hand encapsulating the handle end portion and the intermediate shearing portion to apply rotational force to the tool through the device; and
   (c) a retaining interface means between the handle and the shank encapsulated by the handle adjacent the tool engaging end portion comprising a rotatably interlockable protruding ring and annular channel arrangement between the handle and the shank as to keep the device in one piece upon shearing of the intermediate portion of the shank.

17. The torque limiting device of claim 16, wherein the handle end portion and tool engaging end portion have a cross-sectional configuration other than cylindrical while the cross-sectional configurations of the intermediate shearing portion and the retaining interface means are cylindrical.

18. The torque limiting device of claim 16, wherein the handle end portion of the shank and the encapsulating handle interface therewith form a second strippable shearing portion.

19. The torque limiting device of claim 16, wherein the ring is on the handle and the channel is on the shank.

20. The torque limiting device of claim 16, wherein the ring is on the shank and the channel is on the handle.

21. The torque limiting device of claim 16, wherein the annular channel is surrounded by a collar.

22. The torque limiting device of claim 16, wherein the grippable handle is T-shaped with outwardly extending pegs.

23. The torque limiting device of claim 16, wherein the tool engaging end portion is engageable for rotation with a head of a screw for mounting the medical related tool to an individual.

24. The torque limiting device of claim 23, wherein the tool engaging end has a cross-sectional configuration other than cylindrical.

25. The torque limiting device of claim 24, wherein the head of the screw has a cup the interior of which is cross-sectionally configured to rotatably interlock with the tool engaging end upon insertion of the tool engaging end into the cup.

26. The torque limiting device of claim 16, wherein the medically related tool comprises a halo traction device affixable to a human head with skull screws.

27. A torque limiting device for applying rotational force to a medical related tool, comprising:
  (a) a metallic shank having a handle end portion, an intermediate shearing portion, and a tool engaging end portion, the intermediate shearing portion is adapted to shear the shank into two pieces at a determined rotational force;
  (b) a plastic handle grippable by a human hand encapsulating the handle end portion and the intermediate shearing portion to apply rotational force to the tool through the device;
  (c) a second strippable shearing portion formed between the interface of the handle end portion of the shank and the encapsulating handle; and
  (d) a retaining interface means between the handle and the shank encapsulated by the handle adjacent the tool engaging end portion as to keep the device in one piece upon shearing of the intermediate portion of the shank.

28. The torque limiting device of claim 27, wherein the handle end portion and tool engaging end portion have a cross-sectional configuration other than cylindrical while the cross-sectional configurations of the intermediate shearing portion and the retaining interface means are cylindrical.

29. The torque limiting device of claim 27, wherein the retaining interface means comprises a rotatably interlockable protruding ring and annular channel arrangement between the handle and the shank.

30. The torque limiting device of claim 27, wherein the tool engaging end portion is engageable for rotation with a head of a screw for mounting the medical related tool to an individual.

31. The torque limiting device of claim 30, wherein the tool engaging end has a cross-sectional configuration other than cylindrical.

32. The torque limiting device of claim 31, wherein the head of the screw has a cup the interior of which is cross-sectionally configured to rotatably interlock with the tool engaging end upon insertion of the tool engaging end into the cup.

33. The torque limiting device of claim 27, wherein the medically related tool comprises a halo traction device affixable to a human head with skull screws.

* * * * *

UNITED STATES PATENT AND TRADEMARK OFFICE
CERTIFICATE OF CORRECTION

PATENT NO. :  5,347,894
DATED      :  September 20, 1994
INVENTOR(S) : Paul D. Fischer It is certified that error appears in the above-indentified patent and that said Letters Patent is hereby corrected as shown below:

In column 3, line 48, please delete the word "control", and replace it with --central--.

In column 5, line 5, please delete the numeral "18", and replace it with --46--.

Signed and Sealed this

Third Day of January, 1995

*Attest:*

BRUCE LEHMAN

*Attesting Officer*     *Commissioner of Patents and Trademarks*